United States Patent [19]

Kampner

[11] Patent Number: 4,990,161
[45] Date of Patent: Feb. 5, 1991

[54] IMPLANT WITH RESORBABLE STEM

[76] Inventor: Stanley L. Kampner, 1270 Armsby Dr., Hillsborough, Calif. 94010

[21] Appl. No.: 647,764

[22] Filed: Sep. 6, 1984

Related U.S. Application Data

[63] Continuation-in-part of Ser. No. 590,258, Mar. 16, 1984.

[51] Int. Cl.⁵ ............................................. A61F 2/30
[52] U.S. Cl. ....................................... 623/16; 623/22; 623/23; 623/20
[58] Field of Search ................. 3/1, 1.9, 1.91, 1.911, 3/1.912, 1.913; 128/92 C, 92 CA, 92 G, 92 BC, 92 B, 92 BA, 92 E

[56] References Cited

U.S. PATENT DOCUMENTS

| | | | |
|---|---|---|---|
| 2,112,007 | 3/1938 | Adams | 128/92 B |
| 3,463,158 | 8/1969 | Schmitt | 128/92 BC |
| 3,543,749 | 12/1970 | Grove | 623/16 |
| 3,623,164 | 11/1971 | Bokros | 128/92 B |
| 3,840,904 | 10/1974 | Tronzo | 623/22 |
| 4,120,730 | 10/1978 | Trojer et al. | 623/16 |
| 4,356,572 | 11/1982 | Guillemin et al. | 128/92 G |
| 4,484,570 | 11/1984 | Sutter et al. | 128/92 B |
| 4,488,319 | 12/1984 | Von Recum | 3/1.913 |
| 4,495,664 | 1/1985 | Blanquaert | 3/1.913 |

FOREIGN PATENT DOCUMENTS

| | | | |
|---|---|---|---|
| 2349357 | 4/1975 | Fed. Rep. of Germany | 623/22 |
| 2502884 | 7/1976 | Fed. Rep. of Germany | 3/1.912 |
| 2558446 | 7/1976 | Fed. Rep. of Germany | 3/1.912 |
| 2628284 | 1/1977 | Fed. Rep. of Germany | 3/1.913 |
| 1026789 | 7/1983 | U.S.S.R. | 128/92 CA |
| 4554 | of 1888 | United Kingdom | 128/92 B |

Primary Examiner—David J. Isabella
Attorney, Agent, or Firm—Townsend and Townsend

[57] ABSTRACT

This invention relates to a biodegradable anchor for a permanent implant of a bone joint, e.g. hip, shoulder, knee or finger. The biodegradable anchor is an elongated member which has an exterior surface which tightly engages a cavity in the bone and is substantially immovable within the cavity upon implant. A non-resorbable means of securing the anchor to the permanent implant is also included.

34 Claims, 3 Drawing Sheets

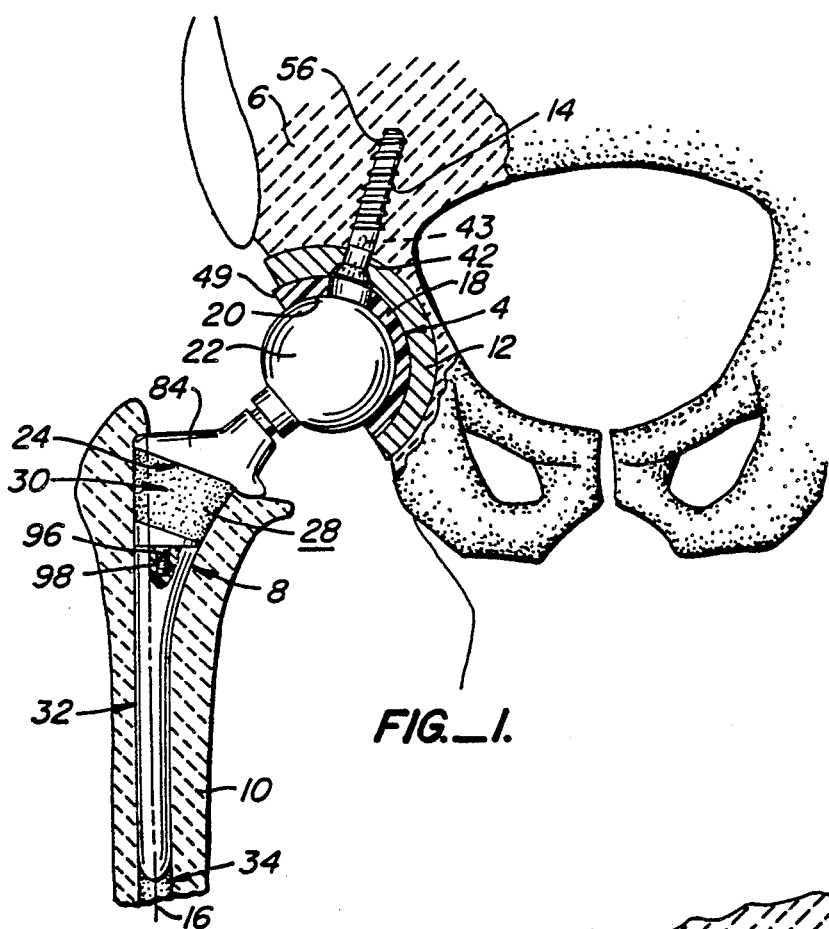
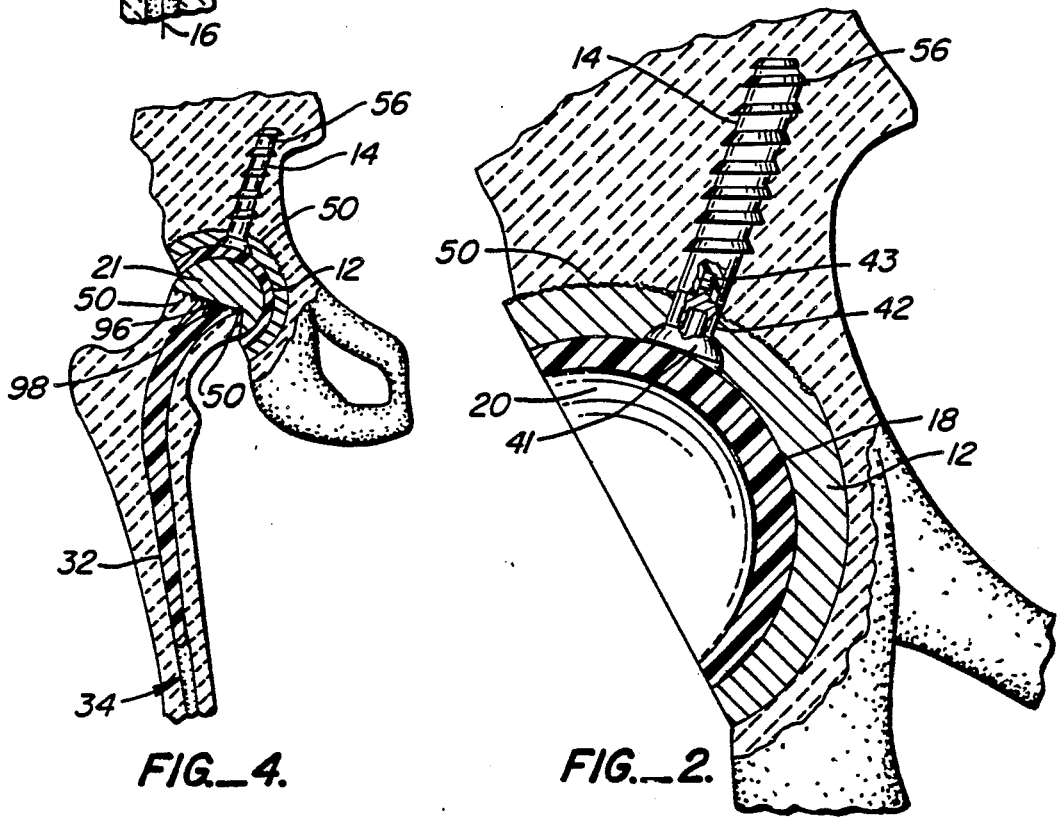
FIG.—1.
FIG.—4.
FIG.—2.

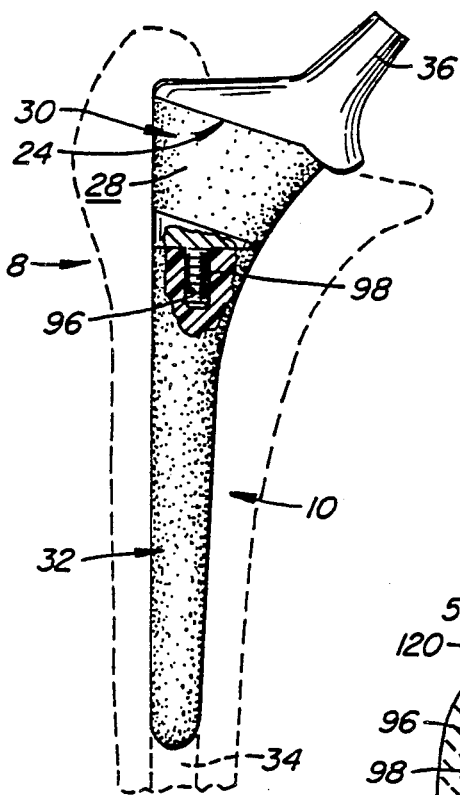
FIG._3.
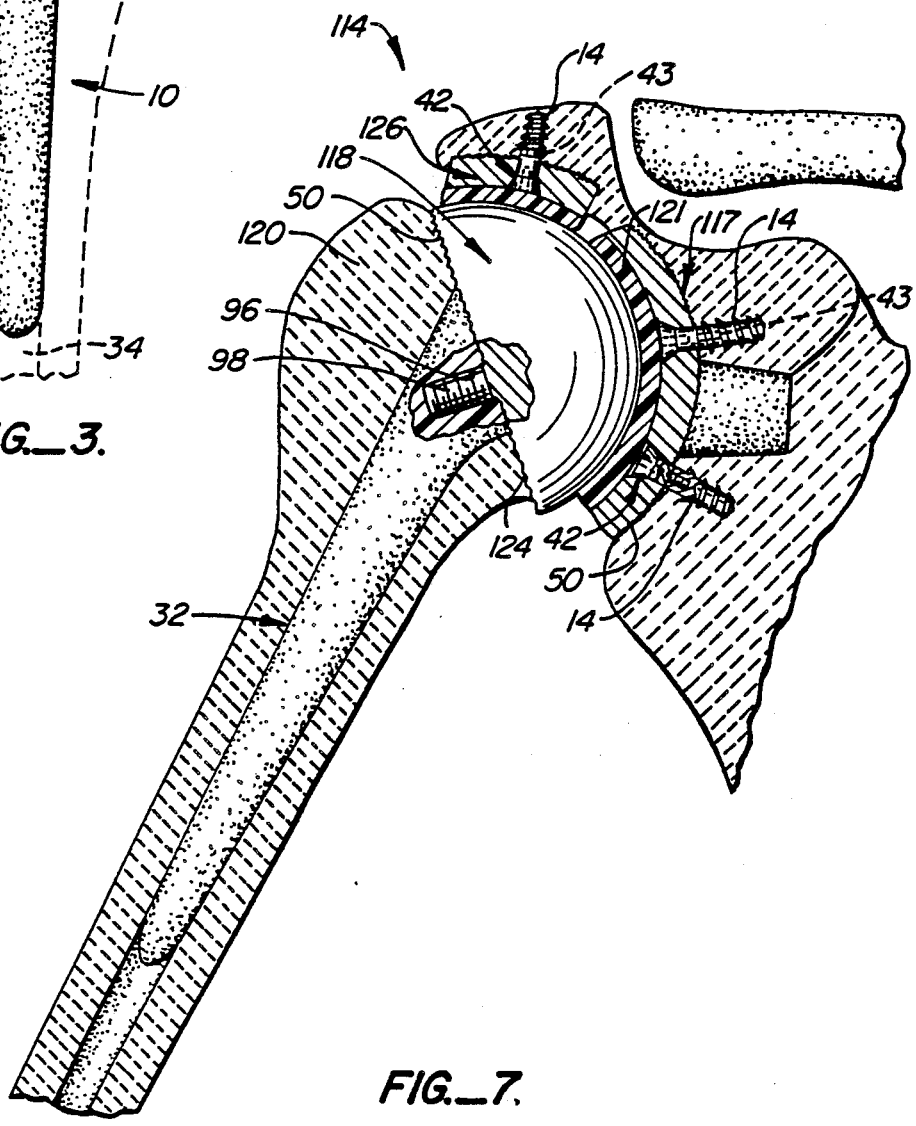
FIG._7.

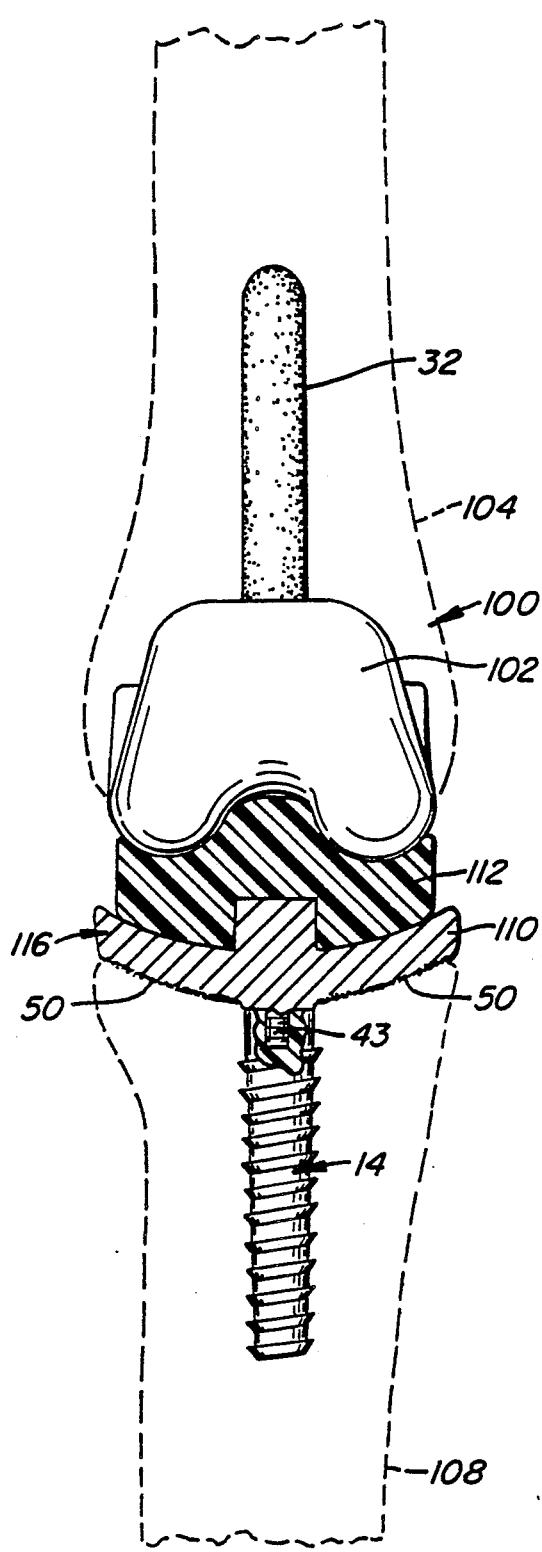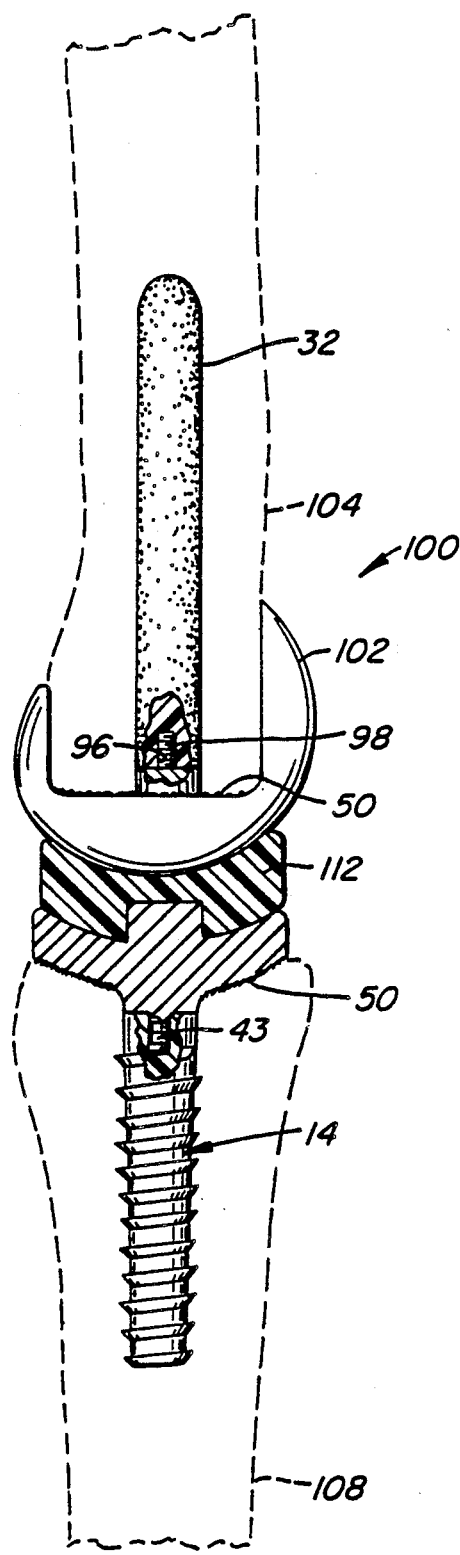

IMPLANT WITH RESORBABLE STEM

This is a continuation-in-part of copending Ser. No. 590,258, filed Mar. 16, 1984.

BACKGROUND OF THE INVENTION

The prosthetic replacement of joints, such as the shoulder, hip, knee, ankle, and wrist has evolved over the years from early, relatively crude models to current prostheses which closely duplicate functions and motions of a natural joint. As a result, prosthetic joints have provided patients with increasing comfort, freedom of motion and an ability to lead nearly normal lives.

Although there have been problems with excessive wear between components of prosthetic devices which move with respect to each other, by and large the fixation of the prosthetic components to the patient's bone structure did and continues to represent the greatest difficulty. Early attempts to solve this problem by use of what were thought to be mechanical locks between the implants and the bone and by use of tissue compatible acrylic cement were discussed in the inventor's copending application, Ser. No. 590,258 filed Mar. 16, 1984.

In cemented implants the cement initially acts as a grout to "form-fit" the implant to the bone. It then "cold-cures" to a hard material which mechanically fixes itself to the bone by interdigitating into the bone trabeculae. This ability of the cement to fix a metal or plastic implant component securely to bone is the main factor which has so greatly improved the status of joint replacement over the prior state of merely implanting the component into bone and hoping that it actually stayed securely in place. Most of the components implanted without cement were not securely fixed and ultimately came loose in the bone with subsequent pain and failure of the procedure. Thus, cement fixation of implants gives excellent short-term results; however, in younger, heavier, or more active individuals, the bond between bone and cement eventually broke down. The result was a loosening or separation between the cement-bone-implant interface which placed the device back into a category similar to implanted devices prior to use of cement-fixation, i.e., the implant was not securely fixed to the bone and pain which indicated a failure of the procedure was the end-result.

As a consequence of increasing numbers of failures with cemented devices, alternative methods of fixation of the implant were sought. One alternative, which is currently the state of the art for implant fixation, is to coat the surface of the implant with a porous material to allow the patient's bone to grow into the pores, thereby biologically fixing the implant to the bone. This appears to be the ideal method of implant fixation. The patient's own tissue now holds the implant and the latter has become a permanent part of the bone, thus obviating the problem of implant loosening.

Another problem encountered with joint implants is an abnormal stress transference from the implant to the bone. The ideal stress transference of load to the bone is the normal, anatomical transference. To approximate it, the implant material should have mechanical properties similar to those of the bone and should replace only the destroyed joint surface. This would place no implant material, or only a minimal amount of implant material, within (intramedullary) the bone. This is most difficult to do with joints having porous implant surfaces because they require immediate rigid fixation for a sufficient time period to assure at least six to twelve weeks in growth time. If the device is not held rigidly, there will be micro-motion occurring at the implant-bone surface which results in a fibrous tissue in-growth rather than the necessary securely-fixed bony in-growth. The currently most common method of holding the implant rigidly in the bone is by providing the implant with a stem which "press-fits" into the intramedullary cavity of the bone, e.g., the femur, or if no such cavity is present, by anchoring the implant to the bone, e.g., the pelvis, with a threaded anchor bolt. Such a press-fit of the stem into the shaft of the bone holds the device rigidly and allows an adequate bone in-growth for secure fixation. For the surgeon it also provides the desired proper anatomical placement of the implant in the bone in a reproducible manner.

The short coming of the aforesaid approach is that loading of the bone is no longer physiologic. Instead of being loaded primarily at the end of the bone near the joint surface as in the normal situation, the bone becomes loaded more distally in the shaft where the stem of the implant is fixed to the bone. The result is an abnormal transference of stress which bypasses or "unloads" the end or joint surface portion of the bone, with a subsequent resorption of that bone. This leads to a weakening of bone in that area over a period of years, thus creating the potential for fracture or disappearance of the bone that previously held the implant securely. The result is again a loosening of the implant within the bone with all the adverse consequences previously mentioned.

For implants, such as an acetabular cup of a hip prosthesis, which are vertically held in place with a screw, the non-physiologic transference of stresses is less pronounced because the location and orientation of the anchoring bolt can be selected to minimize non-natural load transference stresses. Nevertheless, at the very least the presence of the anchoring bolt in the bone weakens the latter and is undesirable for that reason alone.

Thus, if a stem placed down the medullary cavity of the bone (for a correct alignment of the implant and for its immediate, rigid fixation to allow bony in-growth fixation) produces an abnormal stress distribution, it would appear obvious to utilize an implant without a stem. In such a case the implant would essentially only resurface the destroyed articular surface. This is more readily done in joints, such as the knee, elbow, or ankle, than in others, such as the hip, shoulder or wrist. However, even if a stemless implant is feasible, its immediate rigid fixation is not as secure as if the implant were anchored with a stem, or an anchor bolt. When the stem functions to correctly align an anchor or an anchor bolt in its correct position until bone in-growth is complete, an alternative mechanism is necessary therefore to accomplish the functions of the stem. One such mechanism could be a transcortical fixation of the implant such as multiple screws. This, however, makes it more difficult for the surgeon to correctly and reproducibly position and align the implant.

SUMMARY OF THE INVENTION

As the foregoing discussion demonstrated, some types of stem or screw mechanisms are highly desirable even if not absolutely essential to correct alignment and adequate anchoring of the implant while bony ingrowth occurs at the porous implant surfaces. The most ideal biomechanical solution, from the standpoint of physiologic transference of stresses across the joint to the bone, would be to implant a stem or an anchor bolt which would disappear once it has served its function. This is accomplished in accordance with the present invention by providing a composite implant having an anchoring device, e.g., a stem or an anchor screw, made of a biodegradable, resorbable material and a functional joint component defining the articulating surface of the implant made of a permanent, non-resorbable material, e.g., metal. Selected portions of the implant surface in contact with the bone are porous to limit and direct the bone in-growth to areas of natural load and stress transference.

Once in-growth has occurred and the implant is directly fixed to the bone it is implanted into, the stem is no longer required and it can be permitted to resorb, i.e., disappear. The resorption of the stem material can be programmed to take place over whatever length of time is necessary, i.e., 6 weeks, 8 weeks, 12 weeks, 6 months, 1 year or more, depending on how much time the particular joint or bone involved takes to adequately fix the implant to the bone.

Following the resorption of the stem or anchor bolt, the only remaining permanent portion of the implant in the bone is that portion closest to the joint surface. The biomechanical end-result is that the bone holding the implant is stressed primarily adjacent to the surface as in the normal physiologic situation. There will thus be a near normal transference of stresses to the bone and no unloading of stresses on the bone immediately beneath the implant surface. In essence, the stressed bone will be as close to normal as possible, almost as if no prosthetic joint device had been inserted.

Thus the present invention retains all the advantages of utilizing a stem or anchoring bolt during a prosthetic joint implantation, yet, it eliminates the drawbacks of permanently implanted stems and bolts.

The anchor stems or bolts can be fabricated from a variety of resorbable, biodegradable materials including certain ceramics, such as calcium hydroxyapatite or tricalcium phosphate; polymers such as polyesters of glycolic acid or lactic acid, and polyamides of α-amino acids; and unmodified or modified natural polymers such as gelatin or starch.

The use of biodegradable or resorbable materials as such is known. For example, U.S. Pat. No. 4,356,572 to Guillemin et al. discloses use of a biodegradable bone prosthesis or implant made of a coherent material comprising calcium carbonate in crystalline form. The prosthesis or implant disclosed therein is a filler or replacement part for bone substance.

U.S. Pat. No. 3,899,556 to Heide et al. discloses a process for producing an implantable, porous, ceramic bone substitution or bone connection which has open pores of substantially regular or uniform size, distribution and disposition. The process suggested by Heide et al. includes producing a frame which corresponds approximately to the pores and pore connections of the desired finished product, filling the frame with a physiologically suitable and biologically compatible castable or pourable ceramic mass and after at least a partial hardening of the ceramic mass, dismantling or removing the frame, whereby a finished raw product or ceramic material is obtained.

U.S. Pat. No. 4,195,366 to Jarcho et al. discloses the use of a ceramic material, i.e. whitlockite to fill a void in a bone. A defect or void in the bone is filled with this ceramic either as a shaped body or in particulate form.

U.S. Pat. No. 4,344,190 to Lee et al. suggests the use of a biodegradable plug with a hip implant. The reamed out medullary cavity is filled with cement and the biodegradable plastic plug forms a mold for the cement.

U.S Pat. No. 4,202,055 to Reiner et al. discloses a non-porous outercoating for am implantable prosthesis wherein the coating is composed of a calcium phosphate which is bioactive and at least one polymer which is mechanically and chemically stable in the body. Reiner et al. do not contemplate use of a screw or a bolt of any type.

U.S. Pat. No. 4,192,021 to Deibig et al. discloses the use of a mixture of calcium phosphates and polymers which are biodegradable as an anchoring material.

U.S. Pat. No. 3,929,971 to Roy discloses synthetic materials useful as biomaterials having a microstructure substantially corresponding to the microstructure of porous carbonate skeletal material of marine life and made up of hydroxyapatite or whitlockite.

U.S. Pat. No. 3,787,900 to McGee discloses use of discrete microcrystals of a calcium phosphate compound together with the discrete microcrystals of refractory compound, such as the mineral spinel, aluminum phosphate, or aluminum oxide, as a prosthesis material useful for artificial bones or teeth.

U.S. Pat. No. 3,905,047 to Long discloses use of particles such as alumina and calcium pyrophosphate in a unitary body prosthesis.

U.K. Patent No. 2 072 514 B discloses orthopedic implants composed of biologically inactive biocompatible structural materials and a bioactive control component. The components consist of a layer of brazing or silver solder and the structural material can be titanium and/or titanium alloy and/or cobalt chrome molybdenum alloy. The control component produces a chemical or electrical effect to promote or inhibit bone growth in the region of the prosthetic implant. The implant includes an elongated structural member which is inserted into bone material and the bioactive material is inserted in the region of the inserted end. The device assists or replaces mechanical bone function and the structural member remains in place after the bioactive material has been degraded.

Offenlegungsschrifft De 29 47 875-A discloses granular, corpuscular or chip-like aggregates of organic materials which dissolve in the human body over a period of time and are mixed with a monomer in a reaction-inhibiting protective jacket, and a powdery second component which is reactive with the monomer and further standard additives to form a cement composition useful in prosthesis.

However, the prior art nowhere suggests to employ biodegradable materials for temporarily fixing bone implants until bony in-growth into a porous surface of the implant has been achieved.

BRIEF DESCRIPTION OF THE DRAWINGS

FIG. 1 is a schematic, front elevational view through a human hip joint, illustrating the pelvis and the upper portion of the femur, and shows a prosthetic hip constructed in accordance with the present invention immediately following insertion;

FIG. 2 is an enlarged cross-sectional view of the acetabular component of the prosthetic hip illustrated in FIG. 1;

FIG. 3 is a front elevational view of the righthand femoral component of the prosthetic hip illustrated in FIG. 1;

FIG. 4 is a schematic, front elevational view through a human hip joint, illustrating an alternate embodiment of a prosthetic hip constructed in accordance with the present invention;

FIG. 5 is a schematic, front elevational view of a human knee joint, illustrating the lower portion of the femur and the upper portion of the tibia, and shows a prosthetic knee constructed in accordance with the present invention immediately following insertion;

FIG. 6 is a lateral side elevation of the prosthetic knee illustrated in FIG. 5; and FIG. 7 is a schematic, front elevation through a human shoulder, illustrating the scapula and the upper portion of the humerus and shows a prosthetic shoulder constructed in accordance with the present invention immediately following insertion of the prosthetic shoulder.

DETAILED DESCRIPTION OF THE PREFERRED EMBODIMENT

Referring first to FIG. 1 a total prosthetic hip 2 constructed in accordance with the present invention comprises an acetabular component 4 fixed to a patient's pelvis 6 and a femoral component 8 attached to the patient's femur 10. FIG. 1 and FIG. 2 illustrate the acetabular component which is defined broadly by an acetabular cup 12 connected to a biodegradable, resorbable anchor bolt 14 threaded into the pelvis along the pectineal line at an inclination of approximately 20° relative to the longitudinal axis 16 of the femur.

The cup is constructed of an non-corroding, non-resorbable, high strength material such as a cobalt-chromium alloy or a titanium alloy. Disposed within the cup is a low friction liner or insert 18 which defines a spherically shaped acetabular socket 20 that movably receives a ball 22 attached to the femoral implant 8. The cup includes a fixation hole or bore which is positioned so that, upon implementation of the cup, the bore is aligned with the pectineal line of the patient's pelvis. The bore includes a recess which defines an inwardly facing shoulder that, upon implantation, is engaged by a set screw 42 having a threaded end 43 which extends into and engages the anchor bolt 14. The set screw is non-resorbable and acts as an interconnection between the resorbable anchor bolt 14 and the non-resorbable cup 12.

The cup also has an exterior porous surface area 50 which surrounds the bore and promotes bone in-growth in the area of load transfer between the pelvis and the cup. To achieve the desired bone in-growth, the pores are preferably of a size in the range of between about 250–450$\mu$. The remainder of the exterior cup surface is smooth to inhibit bone in-growth thereover. The exact dimensioning of the porous surface 50 is not critical.

To prevent any potential toxic effect of increased ion transfer as a result of the increased surface area about the porous surface 50, at least the porous surface area can be coated with a thin impervious layer, including methylmethacrylate cement, carbon, calcium hydroxyapatite and tricalcium phosphate. Such coatings are made commercially according to methods which are unknown to applicant and which applicant believes are maintained as a trade secret.

Resorbable anchor bolt 14 has a first end with external thread 56 formed to cut into and firmly engage the bone structure. The opposite, free end of the anchor bolt includes an internal thread which is engaged by set screw 42. The anchor bolt is fabricated from a resorbable material such as biodegradable ceramics, modified or unmodified natural polymers, such as starch or gelatin, polymers such as polyesters of glycolic acid or lactic acid and polyamides of $\alpha$-amino acids, etc. The material is selected to resorb at a predetermined time. For most applications this will coincide with a time period sufficient to allow mature bony in-growth about the cup for adequate mechanical fixation of the implant to the pelvis.

During implantation, the resorbable anchor bolt is aligned with the bone in the cup so that the set screw 42 can be tightened to firmly secure the cup to the anchor bolt and thereby, to the bone.

After implantation, the insert may be positioned so that an overhanging portion 49 protrudes beyond the cup as shown in FIG. 1. This provides for a better seating of the associated ball over a wider range of motions and helps prevent accidental dislocations of the ball and the socket.

Referring now to FIGS. 1, and 3, the construction and implantation procedure for the femoral component 8 is discussed in detail. To enable the implantation of the hip prosthesis to the femoral component 8, the head and neck of the femur 10 are initially resected to form an exterior femoral face 24 which is planar, generally perpendicular to a pectineal line and is at an angle of approximately 70° to the longitudinal femur axis 16.

The femoral implant includes an intertrochanteric body 28 with a non-resorbable male screw 98 depending therefrom. The intertrochanteric body is press-fit into a correspondingly shaped and appropriately dimensioned intertrochanteric, upwardly opening cavity 30 in the femur. A resorbable stem 32 extends downwardly from the body into the medullary cavity 34 of the femur. The femoral component further has a neck 36 on its medial side which extends generally upwardly and in a medial direction and to which is mounted the ball 22 that cooperates with the socket 20 of the acetabular component. The resorbable stem 32 acts as a guide to ensure proper placement of the femoral component in the intertrochanteric body and keeps it there until bony in-growth has fixed the body to the femur.

The stem is fabricated from a biodegradable, resorbable material including polylactic acid, ceramics, etc. and is connected to the intertrochanteric body by a female thread 96 located on the stem which cooperates with a corresponding non-resorbable male screw 98 depending from the intertrochanteric body. Locating the female thread 96 in the stem section prevents the formation of stress concentrations in the intertrochanteric body. The interconnection between intertrochanteric body and the stem typically is in the region of the stem where it straightens out in the lateral plane, although it may also be located at other sites along the stem.

Once the femoral implant is firmly fixed by bony in-growth in its proper position, the function of the stem section is over and it is eliminated by resorption. The final result is a stemless femoral component that allows a more physiologic transference of stresses to the proximal femur as opposed to a stemmed implant where there is the potential for fixation distally, thereby potentially causing stress shielding and bone resorption proximally with an increased chance of mechanical failure.

Turning now to the implantation procedure for the femoral component, the head and neck of the femur are first resected to form the external femoral loading face 24 and the intertrochanteric cavity 30 is then shaped by removing soft (non-load bearing) bone tissue. The entire intertrochanteric cavity is broached slightly undersize relative to the implant body to achieve a press-fit therewith.

Prior to implanting the stem is connected to the intertrochanteric body by screwing the body into the stem. Next, the femoral component is implanted by placing the stem into the medullary cavity and then pressing the intertrochanteric body 28 into the intertrochanteric cavity until the internal and external loading surfaces firmly engage the bone.

During the implantation process the elongated stem acts as a guide to prevent an accidental misalignment of the intertrochanteric body during the insertion step, particularly when substantial forces must be applied to overcome the press-fit between the body and the cavity. Once inserted, however, the stem has no significant function. In the design of the present invention with its resultant stemless implant, there are no distal stresses, as seen in the normal femur. The absence of such stresses about the femoral cortex adjacent to the stem, coupled with the transfer of loads at the internal and external loading surfaces assures that the femoral implant is top loaded in a manner analogous to the physiological loading of a femur in a healthy hip joint.

Referring now to FIG. 4, an alternate embodiment of a femoral implant in accordance with the present invention is illustrated. The alternate femoral implant is composed of a generally semicircular non-resorbable femoral head component 21 which is chosen to fit into cup 12 upon implant. Non-resorbable male screw 98 is attached to and protrudes from the generally planar surface of the femoral head component 21. Porous surface 50 promotes bone in-growth. Resorbable stem 32 with internal thread 96 is engaged by non-resorbable screw 98. After resorption the bone will totally surround male screw 98.

Referring now to FIG. 5 a prosthetic knee 100 having a resorbable anchor and a resorbable stem is shown and illustrates a non-resorbable femoral component 102 fixed by a resorbable stem 32 to a patient's femur 104 and a tibial component 116 attached by a resorbable anchor 14 to the patient's tibia 108. Broadly speaking, the tibial component is defined by a tibial cup 110 which is connected to a resorbable anchor bolt 14 threaded into the tibia. The tibial cup is constructed of a non-resorbable, high strength material preferably a metal such as cobalt-chromium alloy or a titanium alloy, for example. Non-resorbable, externally threaded set screw 43 serves as an interconnection between the non-resorbable tibial component and the resorbable anchor bolt 14 in a manner similar to that of set screw 43 in the hip prosthesis. Cup 110 includes a bone for the set screw and an exterior porous surface area 50 which surrounds the bore and promotes bone in-growth in the area of load transfer between the tibia and the cup. To prevent potential toxic effect of increased ion transfer as a result of the increased surface area about the porous surface 50, at least the porous surface area can be coated with a thin impervious layer.

Referring now to FIGS. 5 and 6, the femoral implant includes a non-resorbable femoral component 102, having porous coating 50, and a non-resorbable male screw 98. A resorbable stem 32 is attached to the femoral component with a female thread 96 on the resorbable stem which cooperates with a corresponding non-resorbable male screw 98 extending from the femoral component. The resorbable stem acts as a guide to prevent an accidental misalignment during implantation, thereafter it holds rigidly to allow bony fixation into the porous coating. A component 112, preferably plastic, is interposed between the tibial component and the femoral component. After resorption, screw 98 and screw 43 will be surrounded by bone so that the implant will not become loose or rattle.

Referring to FIG. 7 wherein a schematic front elevation through a human shoulder of a prosthetic shoulder 114 having resorbable anchors and a resorbable stem in accordance with the present invention is shown immediately after insertion of the prosthetic shoulder and following resorption of the anchor devices. The prosthetic shoulder 114 comprises a glenoid component 117 and the acromial component 126 fixed to a patient's shoulder and a humeral component 118 attached to the patient's humerus 120. Broadly speaking, the glenoid component and the acromial component are defined by a cup 121 which is comprised of a plastic insert with a metal backing. The cup has a substantially semi-spherical configuration and is secured to the scapula with one or more non-resorbable set screws 42 which are threaded into resorbable anchor bolts 14. Disposed within the cup is a low friction socket that movably receives the humeral head component 118. Cup 121 includes an exterior porous surface area 50 which surrounds the bore through which the set screw extends to promote in-growth in the area of load transfer between the shoulder and the cup. To achieve the desired bone in-growth, the pores are preferably of a size in the range between about 250–450μ. To prevent any potential toxic effect as the result of the increased surface area about the porous surface, at least the porous surface areas can be coated with a thin impervious layer of material, such as methylmethacrylate cement, carbon, calcium hydroxyapatite or tricalcium phosphate.

To enable the implantation of the shoulder prothesis to the humeral component, the head and the neck of the humerus are resected to the form humeral face 124 which is planar. A non-resorbable semi-circular humeral head component 118 having porous surface area 50 with a male screw 98 depending therefrom is provided. A resorbable stem 32 which has a corresponding female thread 96 located therein is attached to the humeral head component. The stem acts as a guide to prevent accidental misalignment during implantation. Once the humeral implant is firmly fixed by bony in-growth in its proper position, the fixation function of the stem is over and it is eliminated by resorption. The final result is a stemless humeral component that allows a more physiological transference of stresses to the humerus.

With respect to all prosthetic implants of the present invention, there remains a permanent male thread or screw which protrudes into the bone after resorption of the anchoring device. After resorption of the anchor, the bone has grown back and surrounds the non-resorbable permanent anchor or screw so that the implant does not come loose or rattle. Although hip, shoulder and knee replacement has been described with particularity, it should be understood that the present invention is not so limited. Resorbable anchors of the present invention are applicable to all joints including wrist, finger, elbow, ankle, foot and toe.

What is claimed is:

1. An anchor for a permanent implant for a bone joint comprising an elongated member for insertion into a bone cavity for fixing the implant relative to the bone, the member being constructed substantially entirely of a biodegradable material so that the member can resorb after a period of time, the member having an exterior surface shaped to tightly engage the cavity and to be substantially immovably disposed within the cavity after being placed therein, and means for securing the member to the permanent implant.

2. An anchor according to claim 1 wherein the securing means comprises a threaded hole in the member.

3. An anchor according to claim 1 wherein the exterior surface defines a male thread.

4. An anchor according to claim 1 wherein the exterior surface is substantially smooth.

5. An anchor according to claim 1 wherein the exterior surface is shaped to tightly fit into a canal defined by a natural bone.

6. An anchor according to claim 2 wherein the threaded hole is engageable with an externally threaded screw engaging a surface of the permanent implant.

7. An anchor according to claim 1 wherein the biodegradable material is selected from the group consisting of polyesters of glycolic acid, polyesters of lactic acid, polyamides of α-amino acids, unmodified polymers, modified polymers, calcium hydroxyapatite, tricalcium phosphate or polylactic acid.

8. An anchor according to claim 1 wherein the permanent bone implant is selected from an alloy of cobalt-chromium or titanium.

9. An anchor according to claim 1 wherein the implant is part of a prosthetic hip.

10. An anchor according to claim 1 wherein the implant is part of a prosthetic knee.

11. An anchor according to claim 1 wherein the implant is part of a prosthetic shoulder.

12. An anchor according to claim 1 wherein the elongated member is a threaded bolt and the securing means include a screw engaging the permanent implant threading into the bolt.

13. An anchor according to claim 1 wherein the elongated member is a stem having an exterior surface that is substantially smooth and wherein the securing means comprises a threaded hole in the stem and a screw engaging the permanent implant for threading into the hole in the stem.

14. A procedure for the implantation of a prosthetic implant comprising the steps of:
 a. providing a functional implant component adapted to remain in permanent contact with the bone;
 b. forming a portion of the component in contact with the bone so that bony ingrowth can attach directly thereto;
 c. opening a cavity in the bone;
 d. placing the functional component against the bone;
 e. inserting an anchor substantially completely constructed of a resorbable material into the cavity so that the anchor is substantially immovably disposed within the cavity;
 f. fixedly securing the component to the anchor so that the component is in contact with bone surrounding the cavity;
 g. growing bone proximate the cavity into the portion of the component to thereby permanently fix the component to the bone; and
 h. substantially completely resorbing the anchor after the completion of the promoting step so that natural tissue can grow back into the cavity.

15. A prosthetic implant for a bone joint comprising a component defining an operative portion of the joint, the component having an interface facing generally away from the joint and adapted to be placed into intimate contact with a natural bone to which the component is to be fixed, at least part of the interface including means promoting bony ingrowth when the interface is in intimate contact with the natural bone; an anchor connected to the component adapted to be inserted in a cavity in the bone for orienting and immovably fixing the component to the bone immediately upon implantation, the anchor being constructed of a biodegradable material so that it resorbs after a period of time and thereby vacates the cavity to permit natural bone to grow back into the cavity.

16. An implant according to claim 15 including means for removably securing the anchor to the component.

17. An implant according to claim 15 wherein at least part of the cavity is a natural bone canal, and wherein the anchor has a smooth exterior surface.

18. An implant according to claim 15 wherein the cavity is a hole drilled in the bone, and wherein the anchor has an exterior surface defining a male thread adapted to threadably engage the hole in the bone.

19. An implant according to claim 15 wherein the component comprises a joint socket, wherein the anchor comprises a male threaded member adapted to threadably engage the cavity, and including means for securing the socket to the member.

20. An implant according to claim 19 including a plurality of threaded members for securing the socket to the bone.

21. An implant according to claim 15 wherein the component comprises a member having a convex exterior configuration adapted to cooperate with a concave joint member.

22. An implant according to claim 21 wherein the convex joint member comprises a ball joint member.

23. An implant according to claim 22 wherein the component further includes a body connected with the ball and defining the interface.

24. An implant according to claim 23 wherein the body and the ball are detachable secured to each other.

25. An implant according to claim 22 wherein a portion of the ball which faces the concave member has a generally spherical configuration, and wherein a portion of the ball which faces away from the concave member defines the interface.

26. An implant according to claim 25 wherein the interface includes a planar surface adapted to be placed into direct contact with a corresponding planar surface formed on the natural bone to which the implant is to be attached.

27. A procedure according to claim 14 wherein the step of opening a cavity comprises the step of broaching an existing canal in the bone, and wherein the step of inserting an anchor includes the step of forming a press-fit between the anchor and the cavity to thereby substantially immovably fix the anchor and thereby the functional implant to the bone.

28. A procedure according to claim 14 wherein the step of opening a cavity comprises the step of drilling a hole in the bone.

29. A procedure according to claim 28 wherein the step of inserting an anchor comprises the step of threadably engaging the anchor with the hole in the bone.

30. A procedure according to claim 14 wherein the step of forming comprises the step of constructing the functional implant component so that it has a surface which permits bony ingrowth into the component.

31. A procedure according to claim 14 wherein the step of resorbing includes the step of predetermining the length of time required for the anchor to substantially completely resorb.

32. A procedure for replacing a diseased natural joint component on a bone with a prosthetic joint component comprising the steps of: removing the diseased joint component and forming a load transference surface on the bone relatively proximate the diseased joint, providing the prosthetic joint component with an interface adapted to be placed into intimate contact with the load transference surface on the bone and forming at least a portion of the interface to promote bony ingrowth; bringing the interface of the prosthetic join component into intimate contact with the load transference surface on the bone, forming a cavity in the bone which communicates with the prosthetic component when the latter is in contact with the load transference surface, substantially immovably positioning an anchor in the cavity, substantially immovably attaching the prosthetic joint component to the anchor to retain the interface in contact with the load transference surface and to thereby promote bony ingrowth in to the portion of the interface while enabling use of the joint, and permitting the anchor to resorb after bony ingrowth into the portion of the prosthetic component interface has immovably fixed the prosthetic component directly to the bone; whereby load transference from the component to the bone takes place in the vicinity of the joint and is prevented from taking place in the cavity at locations relatively remote from the joint.

33. A prosthetic implant for a bone joint comprising a component defining an operative portion of the joint, the component having a interface facing generally away from the joint and adapted to be placed into intimate contact with a natural bone to which the component is to be fixed, a part of the interface being adapted to directly connect to the natural bone when it is brought into intimate with the natural bone; an anchor connected to the component adapted to be inserted in a cavity in the bone for orienting and immovably fixing the component to the bone immediately upon implantation, the anchor being constructed substantially entirely of a biodegradable material so that it resorbs after a period of time and thereby vacates the cavity to permit natural bone to grow back into the cavity.

34. Procedure for replacing a diseased, natural joint component of a bone with a prosthetic joint component comprising the steps of: removing the diseased joint component and forming a load transference surface on the bone relatively proximate the diseased join; providing a prosthetic joint component with an interface adapted to be placed into intimate contact with the load transference surface on the bone; adapting at least a portion of the interface so that it establishes a direct connection between such portion and the natural bone when it is brought into intimate contact with the natural bone; bringing the interface of the prosthetic joint component into intimate with the load transference surface on the bone; forming a cavity in the bone which communicates with the prosthetic component when the latter is in contact with the load transference surface; substantially immovably positioning an anchor in the cavity; substantially immovably attaching the prosthetic joint component to the anchor to retain the interface in contact with the load transference surface and to thereby promote the establishment of a direct connection between the portion of the interface and the load transference surface while enabling use of the joint; and permitting the anchor to resorb after the direct connection between the portion of the prosthetic component interface and the load transference surface has immovably fixed the prosthetic component directly to the bone; whereby load transference from the component to the bone takes place in the vicinity of the joint and is prevented from taking place in the cavity at locations relatively remote from the joint.

* * * * *